United States Patent [19]

Messing et al.

[11] 4,246,349

[45] Jan. 20, 1981

[54] STABILIZATION OF IMMOBILIZED BACTERIA

[75] Inventors: Ralph A. Messing, Horseheads; Robert A. Oppermann, Painted Post; William S. Ramsey, Corning; Milton M. Takeguchi, Big Flats, all of N.Y.

[73] Assignee: Corning Glass Works, Corning, N.Y.

[21] Appl. No.: 939,176

[22] Filed: Sep. 5, 1978

[51] Int. Cl.³ .............................................. C12N 11/14
[52] U.S. Cl. .................................... 435/176; 435/174; 435/260
[58] Field of Search ............... 195/59, 63, 68; 426/61; 435/176, 174, 260

[56] References Cited

U.S. PATENT DOCUMENTS 4,153,510  5/1979  Messing et al. ..................... 195/59

OTHER PUBLICATIONS

Douglas et al., In-Use Evaluation of Commercially Available Set of Quality Control Cultures, Applied Microbiology, vol. 25, No. 2, Feb., 1973, (pp. 230-234).
Stadhouders et al., Preservation of Starters and Mass Production of Starter Bacteria, Neth. Milk Dairy J., vol. 23, 1969, (pp. 182-199).

*Primary Examiner*—David M. Naff
*Attorney, Agent, or Firm*—William E. Maycock; Clinton S. Janes, Jr.

[57] ABSTRACT

Bacteria immobilized by adsorption on an inorganic carrier are stabilized by carrying out the adsorption procedure in the presence of from about 1 to about 20% weight per volume of sucrose of nonfat dry milk solids and lyophilizing the adsorbed bacteria.

8 Claims, No Drawings

STABILIZATION OF IMMOBILIZED BACTERIA

BACKGROUND OF THE INVENTION

The frequent evaluation of bacteriological procedures, media, and biochemical reagents is mandatory in diagnostic microbiology laboratories to insure the correct identification of pathogenic microorganisms in clinical specimens. The accurate determination of antibiotic susceptibility also is highly dependent upon the routine standardization of media, antibiotic-impregnated discs, and procedures.

To assure the necessary high standards of media reliability and reproducibility in such laboratories, a supply of bacterial cultures which provides appropriate reactions is required. Such laboratories, therefore are confronted with the task of maintaining bacterial control cultures for quality control purposes. Currently, transfer on solid media and lyophilization are common practices used to maintain such control cultures. The disadvantages of such practices include the possible mutation and/or contamination of cultures, potential aerosolization of viable organisms from lyophilized cultures the need for expensive equipment, and the need for technical personnel. See, e.g., G. W. Douglas et al., Appl. Microbiol., 25, 230 (1973).

Recently, such problems have been lessened by the availability of commercial bacterial control cultures such as Bact-Chek ® (Roche Diagnostics, Nutley, N.J.) and Bactrol Disks (Difco Laboratories, Detroit, Mich.). Unfortunately, such commercial bacterial control cultures in general do not include those bacterial species such as *Haemophilus influenzae* and *Neisseria gonorrhoeae* whose viability is difficult to maintain in vitro.

While such commercial bacterial control cultures also can be employed in industrial and research laboratories, such cultures do not appear to be readily adapted for use in industrial processes which utilize one or more biochemical conversions. This is especially true since many industrial processes more and more frequently are utilizing immobilized microbes. Thus, there is a growing need for immobilized process starter bacteria of constant and well-defined composition, whereby the biochemical conversions employing such immobilized bacteria can be optimized by the proper choice of bacteria. Immobilized bacteria having a known and constant composition also are required in the area of biochemical oxygen demand (BOD) determinations. The particular BOD reading which is obtained from such a determination is, to a large extent, dependent upon the nature of the bacteria employed. Since a company discharging waste into a stream can be fined on the basis of the BOD number, the number obtained becomes of critical importance. In addition, the generally unavailability of immobilized bacteria having a known and constant composition and adapted specifically for BOD determinations makes it extremely difficult to correlate BOD numbers obtained by various laboratories, even when efforts have been made to employ the same bacterial species.

SUMMARY OF THE INVENTION

It therefore is an object of the present invention to provide a method for stabilizing immobilized bacteria. This and other objects will be apparent to those skilled in the art from a consideration of the specification and claims which follow.

Accordingly, the present invention provides, in a method of immobilizing bacteria on an inorganic carrier by adsorption, the improvement which comprises carrying out the adsorption procedure in the presence of from about 1 to about 20% weight per volume of sucrose or nonfat dry milk solids.

The present invention also provides a method of stabilizing immobilized bacteria which comprises the steps of:

A. suspending the bacteria to be immobilized in an aqueous medium containing from about 1 to about 20% weight per volume of sucrose or nonfat dry milk solids;

B. mixing the suspension resulting from step A with inorganic carrier;

C. incubating the mixture obtained in step B; and

D. lyophilizing the incubated mixture from step C.

The present invention further provides a method of stabilizing immobilized bacteria which comprises the steps of:

A. suspending the bacteria to be immobilized in an aqueous medium containing from about 1 to about 20% weight per volume of sucrose or nonfat dry milk solids;

B. mixing the suspension resulting from step A with inorganic carrier;

C. incubating the mixture obtained in step B;

D. removing excess liquid from the incubated mixture from step C; and

E. lyophilizing the solid residue remaining from step D.

Immobilized bacteria, when stabilized in accordance with the present invention, are capable of being stored for extended periods of time, especially when stored at a temperature of about 4° c. Such stabilized immobilized bacteria are useful as bacterial control cultures, industrial biochemical process starter bacteria, and as the source of bacteria for biochemical oxygen demand determinations.

DETAILED DESCRIPTION OF THE INVENTION

As used herein, the term "stable", and variations thereof, has reference not only to viability, but also to all standard biochemical and growth characteristics. That is, the term "stable" is used herein to denote that long-term storage does not affect the viability or biochemical and growth characteristics of the organism. The term also refers to no change upon storage in the antibiotic susceptibility profile or pattern of the organism.

The nature of the aqueous medium in which the bacteria are suspended is not critical. Such aqueous medium can be simply distilled water or such medium can be a nutrient broth or similar soultion. As a practical matter, the use of a nutrient broth is perhaps simpler, since it eliminates the need for additional solutions.

As already indicated, the stabilizing agents are sucrose and nonfat dry milk solids. The concentration of the stabilizing agent is not critical, provided that such agent is present in the solution at a level of from about 1 to about 20% weight per volume. Preferably, the stabilizing agent is present at a level of from about 4 to about 12%.

In general, the inorganic carriers are materials having available oxide or hydroxide groups. Such materials can be classified in terms of chemical composition as siliceous materials or nonsiliceous metal oxides. Examples of siliceous materials include, among others, glass, silica, wollastonite, silica gel, bentonite, cordierite, and the like. Representative nonsiliceous metal oxides include alumina, hydroxy apatite, and nickel oxide. The siliceous materials are preferred, with cordierite which includes cordierite-silica materials and silica being most preferred. The physical nature of the carrier is not critical. However, porous carriers normally are preferred in order to provide a relatively high biomass per unit mass of carrier.

Typically, the bacteria are immobilized in accordance with well-known procedures; see, e.g., I. Chibata and T. Tosa, *Appl. Biochem. Bioeng.*, 1, 329 (1976); T. R. Jack and J. E. Zajic, *Advances Biochem. Eng.*, 5, 125 (1977); B. J. Abbott, *Advances Appl. Microbiol.*, 20, 203 (1976); and K. Mosbach, Editor, "Methods In Enzymology", Vol. 44, Academic Press, New York, 1976. Briefly, all that is essentially required is the exposure of carrier to an aqueous suspension of the bacteria to be immobilized. If desired, such exposure can be only for a time sufficient to permit adsorption of the bacteria onto the carrier. Alternatively, if the aqueous suspension comprises a nutrient broth, such exposure can be for a longer period of time which will permit some growth of bacteria during the immobilization procedure.

The present invention is further described, but not limited, by the example which follows.

EXAMPLE

Materials and Methods

Bacteria. The bacteria studied are summarized in Table I.

TABLE I

Summary of Bacteria Studied

| Species | Strain |
|---|---|
| Streptococcus pyogenes | ATCC 10389[a] |
| Neisseria gonorrhoeae | CDC F62[b] |
| Haemophilus influenzae | Unknown[c] |

[a]ATCC - American Type Culture Collection, derived from Bact-Chek ® cultures.
[b]Strain received from the Center for Disease Control (Atlanta, Georgia).
[c]Unknown strain from the Corning Glass Works collection (Corning, New York).

Media and Reagents. All bacteriological media employed in the cultivation and identification procedures were obtained from Difco Laboratories, and were prepared in accordance with the accompanying instructions. Tryptic Soy Agar medium was used to cultivate *Streptococcus pyogenes*. *Neisseria gonorrhoeae* was grown on GC medium and *Haemophilus influenzae* was grown on chocolate agar medium. All three bacteria were immobilized in GC broth which had the same composition as GC medium except that agar was omitted, which broth contained the requisite amount of stabilizing agent.

Carrier. The carrier employed was composed of 80% cordierite and 20% alumina and was 18-25 mesh, U.S. Standard Sieve. The carrier was about 60% porous with pore diameters in the range of from about 3 to about 6μ; the average pore diameter was about 4.5μ.

Immobilization Procedure. In accordance with the usual well-known procedures, a suspension of bacteria in GC broth containing the requisite amount of stabilizing agent was prepared; the optical density, at 660 nm, of the suspension was adjusted to 1.0. A 2-ml. aliquot of the suspension was added to a tube containing 1 g. of the carrier. Each tube was incubated for 3 hours at room temperature on a shaker. Excess fluid then was aspirated. After freezing each tube in a mixture of dry ice and acetone for ten minutes, each tube was placed in a freeze-dryer for 18-20 hours. Each tube then was stored at 4° C.

Microbiological Assays. The shelf life of each immobilized culture was determined by the periodic monitoring of the culture of organism viability. Two to five granules of the immobilized culture were incubated for 48 hours in 2 ml. of tryptic soy broth or in 2 ml. of GC broth containing 1% IsoVitaleX Enrichment (Baltimore Biological Laboratory, Cockeysville, Maryland). Each tube then was examined for bacterial growth and purity. Biochemical reactions and antibiotic sensitivity patterns of selected immobilized cultures were determined following recommended procedures; see, e.g., E. H. Lennette et al., Editors, "Manual of Clinical Microbiology", 2nd Edition, American Society for Microbiology, Washington, D.C., 1974, and A. Balows, Editor, "Current Techniques for Antibiotic Susceptibility Testing", Charles C. Thomas, Springfield, Illinois, 1974.

*S. pyogenes*, *N. gonorrhoeae*, and *H. influenzae* were suspended in GC broth containing 12% weight per volume of sucrose and were immobilized on cordierite-alumina for shelf-life studies. The immobilized bacteria then were stored at 4° C. The shelf-life studies are summarized in Table II.

TABLE II

Shelf-Life Studies of Immobilized Bacteria (12% Sucrose), Stored at 4° C.

| | Recovery of Viable Bacteria (Mos.)[a] | | | | | |
|---|---|---|---|---|---|---|
| Bacteria | 1 | 2 | 3 | 6 | 8 | 10[b] |
| S. pyogenes | + | + | + | + | + | + |
| N. gonorrhoeae | + | + | + | + | + | + |
| H. influenzae | + | + | + | + | + | + |

[a]+ denotes viable bacteria.
[b]Test terminated after ten months of storage.

Standard biochemical and growth characteristics of the organisms were determined prior to and following immobilization. In every case, biochemical and growth characteristics were unaffected by immobilization; that is, pre- and post-immobilization reactions were identical, as shown by the data summarized in Table III.

TABLE III

Pre- and Post-Immobilization Biochemical and Growth Characteristics

| | | Test Results | |
|---|---|---|---|
| Organism | Characteristic | Pre-Immobilization | Post-Immobilization[a] |
| Streptococcus pyogenes | Gram Stain | GPC,[b] chains | GPC, chains |
| | Beta-hemolytic on Blood-Agar Medium | + | + |
| Neisseria gonorrhoeae | Gram Stain | GNDC[c] | GNDC |
| | Growth on Thayer-Martin medium | + | + |
| | p-Aminodimethylaniline oxidation | + | + |
| Haemophilus influenzae | Gram Stain | GNB,[d] Small | GNB, Small |
| | Growth on Chocolate Agar Medium | + | + |
| | Growth Requirement: (a) Hemin (X factor) only | NGr[e] | NGr |
| | (b) Nicotinamide-adenine-dinucleotide (V-factor) only | NGr | NGr |

TABLE III-continued

Pre- and Post-Immobilization Biochemical
and Growth Characteristics

| Organism | Characteristic | Test Results | |
|---|---|---|---|
| | | Pre-Immobilization | Post-Immobilization[a] |
| | (c) X plus V factors | Gr[f] | Gr |

[a] 10 months storage
[b] GPC = Gram Positive Coccus
[c] GNDC = Gram Negative Diplococcus
[d] GNB = Gram Negative Bacilli
[e] NGr = No Growth
[f] Gr = Growth It should be noted that the lyophilization procedure does not require that the containers be vacuum-sealed. Thus, repeated sampling of the immobilized bacteria in the vials after the freeze-drying procedure is possible. Furthermore, the general procedure described and claimed herein allows the ready preparation of mixtures of immobilized bacteria of known types and proportions for a variety of uses. For example, a particular industrial biochemical process may require the use of two or more bacterial species. Such a requirement is readily met by the process of the present invention.

The shelf-life of the immobilized bacteria studied herein clearly was exceptional. It should be apparent to one having ordinary skill in the art that the present invention is not limited to those bacteria specifically evaluated. Thus, the present invention is ideally suited for the immobilization of any bacteria, and is especially important for those bacteria whose viability is difficult to maintain in vitro. Examples of such sensitive bacteria include, among others, Streptococcus pyogenes, Neisseria gonorrhoeae, Haemophilus influenzae, Streptococcus pneumoniae, and the like. Anaerobic bacteria, such as Clostridium perfringens and *Bacteroides fragilis*, constitute another group of bacteria for which the method disclosed and claimed herein is especially useful. It should be noted, however, that the method of the present invention clearly will improve the stability of any immobilized bacteria. Obviously, the difference in stability before or after treatment in accordance with the present invention will be less significant for those bacteria which are less susceptible to degradation or loss of viability upon storage.

What is claimed is:

1. A method of stabilizing immobilized bacteria which comprises the steps of:
    A. suspending the bacteria to be immobilized in an aqueous medium containing from about 1 to about 20% weight per volume of sucrose or nonfat dry milk solids;
    B. mixing the suspension resulting from step A with inorganic carrier having available oxide or hydroxide groups;
    C. incubating the mixture obtained in step B whereby the bacteria are immobilized by adsorption on said inorganic carrier; and
    D. lyophilizing the incubated mixture from step C, wherein the bacteria are selected from the group consisting of those bacteria whose viability is difficult to maintain in vitro.

2. The method of claim 1 in which the carrier is a cordierite material.

3. The method of claim 2 in which the aqueous medium contains sucrose.

4. The method of claim 3 in which the sucrose is present at a level of from about 4 to about 12%.

5. A method of stabilizing immobilized bacteria which comprises the steps of:
    A. suspending the bacteria to be immobilized in an aqueous medium containing from about 1 to about 20% weight per volume of sucrose or nonfat dry milk solids;
    B. mixing the suspension resulting from step A with inorganic carrier having available oxide or hydroxide groups;
    C. incubating the mixture obtained in step B whereby the bacteria are immobilized by adsorption on said inorganic carrier;
    D. removing excess liquid from the incubated mixture from step C; and
    E. lyophilizing the solid residue remaining from step D, wherein the bacteria are selected from the group consisting of those bacteria whose viability is difficult to maintain in vitro.

6. The method of claim 5 in which the carrier is a cordierite material.

7. The method of claim 6 in which the aqueous medium contains sucrose.

8. The method of claim 7 in which the sucrose is present at a level of from about 4 to about 12%.

* * * * *